US005627192A

United States Patent [19]
Pearce et al.

[11] Patent Number: 5,627,192
[45] Date of Patent: May 6, 1997

[54] ANTIHYPERLIPIDEMIC/ANTIOXIDANT DIHYDROQUINOLINES

[75] Inventors: Bradley C. Pearce, East Hampton; John J. Wright, Guilford, both of Conn.

[73] Assignee: Bristrol-Myers Squibb Company, New York, N.Y.

[21] Appl. No.: 405,619

[22] Filed: Mar. 15, 1995

Related U.S. Application Data

[62] Division of Ser. No. 48,696, Apr. 16, 1993, Pat. No. 5,411,969.

[51] Int. Cl.$^6$ .................................................. A61K 31/47
[52] U.S. Cl. ................................... 514/311; 514/313
[58] Field of Search ..................................... 514/311, 313

[56] References Cited

PUBLICATIONS

Brown, et al., *J. Lipid Res*, 21:505–517 (1980).
Wright, et al., *A Symposium On Drugs Affecting Lipid Metabolism*, Houston, Tx (Nov. 1989).
Yamaoka, et al., *Yukagaku*, 34:120–122 (1985).
Serbinova, et al., *Free Radical Biology and Medicine*, 10:263–275 (1991).
Santrucek, et al., *Drugs of the Future*, 13:973–996 (1988).
Buckley, et al., *Drugs*, 37:761–800 (1989).
Gwynne, et al. *Am. J. Cardiology*, 62:1B–77B (1988).
Steinberg, *Circulation*, 84:1420–25 (1991).
Steinberg, *Am. J. Cardiol.*, 57:16H–21H (1986).
Dieber–Rotheneder, et al., *J. Lipid Res.*, 32:1325–32 (1991).
Welch, et al., *J. Med. Chem.*, 25: 81–84 (1982).
Pollak–Bar, et al., *Fat Science Proc.*, 16th ISF Congress, 1059–1067 (1983).

*Primary Examiner*—Samuel Barts
*Attorney, Agent, or Firm*—Prabodh I. Almaula

[57] ABSTRACT

The present invention relates to novel dihydroquinolines which are useful for cholesterol lowering and as antioxidant agents. Also provided is a process for preparing the dihydroquinolines of the present invention, pharmaceutical compositions, and a method of treating or inhibiting hypercholesterolemia, hyperlipidemia, atherosclerosis, and LDL oxidation which comprises administering to birds and mammals in need of such treatment an effective amount of a compound of the present invention.

2 Claims, No Drawings

5,627,192

ANTIHYPERLIPIDEMIC/ANTIOXIDANT DIHYDROQUINOLINES

This is a divisional of application Ser. No. 08/048,696 filed Apr. 16, 1993 now U.S. Pat. No. 5,411,969.

BACKGROUND OF THE INVENTION

1. Field of the Invention

The present invention provides novel dihydroquinolines which are effective as LDL lowering agents and which also have antioxidant capacity.

2. Description of Related Art

It is generally recognized that high blood cholesterol levels are significant risk factors in cardiovascular disease.

It has been established that 3-hydroxy-3methylglutaryl coenzyme A reductase (HMGR) is the first rate limiting enzyme in the biosynthetic pathway for cholesterol, that inhibition of HMGR activity results in a decrease in serum total cholesterol and low density lipoprotein (LDL) cholesterol levels, and that a decrease in serum LDL-cholesterol levels is reflected in a reduction of plasma level of apolipoprotein B. (Brown, et al, *J. Lipid Res,* 21: 505–517 (1980)).

Tocotrienols have been shown to suppress HMGR resulting in the inhibition of cholesterol biosynthesis and a subsequent drop in LDL cholesterol, apolipoprotein B, thromboxane $B_2$, platelet factor 4 and glucose levels. (Wright, et al, *A Symposium On Drugs Affecting Lipid Metabolism,* Houston, Tex. (Nov. 1989)).

The tocotrienols are structurally related to the tocopherols (vitamin E) and differ only by possessing unsaturation in the isoprenoid side chain. Like the tocopherols, the tocotrienols have antioxidative activity. (Yamaoka, et al, *Yukagaku,* 34: 120–122 (1985); Serbinova, et al, *Free Radical Biology and Medicine,* 10: 263–275 (1991)).

Active oxygen species are known to play pivotal roles in the genesis of atherosclerotic plaques, thrombotic episodes, ischemic damage, cancer, aging, dementia, and inflammatory conditions. (Sies, H., *Oxidative Stress*; Academic Press, New York, (1985); Santrucek, M., Krepelka, J., *Drugs of the Future,* 13: 73–996 (1988); Steinberg, *Circulation,* 84: 1400–24 (1991)). Of particular interests are the potential protective effects of antioxidants on lipoproteins, since oxidized LDL is thought to be atherogenic. (Buckley et. al., *Drugs,* 37: 761–800 (1989); Gwynne et. al., *Am. J. Cardiology,* 62: 1B-77B (1988)).

PROBUCOL (4,4'-[(1-methylethylidene)bis(thio)]-bis[2,6-bis(1,1-dimethylethyl)] (Lorelco, Marion Merrell Dow) (Formula I) is a hypolipidemic drug, which is also an excellent antioxidant. PROBUCOL inhibits the oxidative modification of LDL both in vitro and in vivo. (Steinberg, *Am. J. Cardiol.,* 57: 16H–21H (1986)). PROBUCOL, however, suffers from bioavailability problems, exhibits only modest reductions in LDL cholesterol, and has undesirable effects on HDL cholesterol.

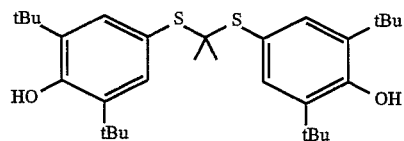

Formula I

Esterbauer et al. (Dieber-Rotheneder, et al., *J. Lipid Res.,* 32: 1325–32 (1991)) have examined the oxidative resistance of LDL as a function of oral vitamin E supplementation. While the oxidative resistance of LDL was significantly enhanced during vitamin E supplementation, antioxidant effectiveness varied considerably from subject to subject.

6-Ethoxy-2,2,4-trimethyl-3,4-dihydroquinoline (ETHOXYQUIN, Tokyo Kasai) is widely used as a feed preservative marketed under the name of SANTOQUIN [Formula II]. This antioxidant chemotype has been incorporated into retinoic acid derivatives, and were evaluated as a cancer-prevention agents. (Welch, et al., *J. Med. Chem.,* 25: 81–84 (1982)). The water soluble analogue MTDQ-DA [Formula III] has been investigated as a antiatherosclerotic drug in cholesterol fed rabbits. (Pollak-Bar, et al., *Fat Science Proc.,* 16th ISF Congress, 1059–1067 (1983)). MTDQ-DA mediated fairly modest effects on various lipid parameters, however this compound completely inhibited plaque progression relative to the cholesterol fed rabbit controls.

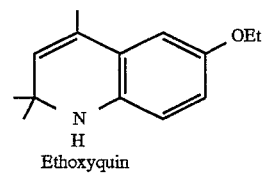

Formula II

Ethoxyquin

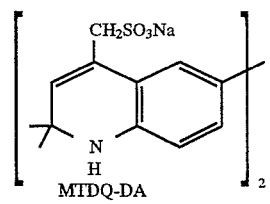

Formula III

MTDQ-DA

While the causative factors in the development of atherosclerosis are many, two important ones are elevated serum cholesterol levels and excessive LDL oxidation.

The above compounds do not successfully unite lipid lowering and antioxidant potential. The present describes the successful union of these two pharmacological properties in dihydroquinolines.

SUMMARY OF THE INVENTION

The present invention provides novel dihydroquinolines which combine lipid lowering with antioxidant effectiveness.

An aspect of the present invention provides dihydroquinolines which are useful for cholesterol/lipid lowering in cases of hypercholesterolemia, hyperlipidemia, atherosclerosis and which are also useful to inhibit LDL oxidation.

Another aspect of the present invention provides a pharmaceutical composition which comprises at least one compound of the present invention and a non-toxic pharmaceutically acceptable carrier.

Another aspect the present invention provides a method of treating hypercholesteremia, hyperlipidemia and thromboembolic disorders in birds and mammals, including humans which consists of administering at least one compound of the present invention to a host in need of such treatment.

Another aspect of the present invention provides a method of inhibiting cholesterol biosynthesis, lowering LDL cholesterol, and inhibiting LDL oxidation in birds and mammals, including humans which consists of administering at least one compound of the present invention to a host in need of such treatment.

Another aspect of the present invention provides intermediates useful for making the dihydroquinolines of the present invention.

These and other advantages and objects of the invention will be apparent to those skilled in the art.

DETAILED DESCRIPTION OF THE INVENTION

The present invention provides compounds of the general Formula IV

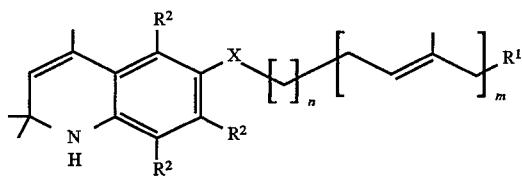

wherein
X is O, S or $CH_2$
$R^1$ is H or

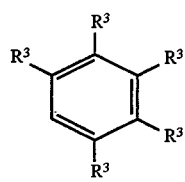

$R^2$ and $R^3$ are independently H, $C_1$–$C_5$ alkyl, $CF_3$, CN, halogen or $OCH_3$,
n is an integer of 0 to 3, and
m is an integer of 1 to 3,
or a pharmaceutically acceptable salt thereof.

As used herein and in the claims, the term "$C_1$–$C_5$ alkyl" is meant to include saturated or unsaturated, branched or straight chain alkyl groups of one to five carbon atoms, including but not limited to methyl, ethyl, propyl, isopropyl, butyl, isobutyl, t-butyl, and the like. The term "halogen" is meant to include fluorine, chlorine, bromine, and iodine.

Also included within the scope of the present invention are pharmaceutically acceptable acid addition salts, the metal salts, and the solvates of the compounds of Formula IV, which may exist in various tautomeric forms.

The synthesis of the farnesylated dihydroquinoline (4) is shown in scheme I. ETHOXYQUIN (Tokyo, Kasai) (1) was dealkylated with hot hydrobromic acid to give the known crystalline phenol (2). This material was bis-acetylated to give the amide-ester intermediate. Selective deprotection with methanolic KOH gave the amide 3. The side chain could be attached by either coupling through a Mitsunobu-type procedure or by direct alkylation. The Mitsunobu procedure was somewhat capricious, and in general the alkylation proved the better method of synthesis. Removal of the amide protecting group was smooth using excess lithium triethylborohydrate. Use of the amide protecting group was not absolutely necessary, however the yields were significantly better in its presence.

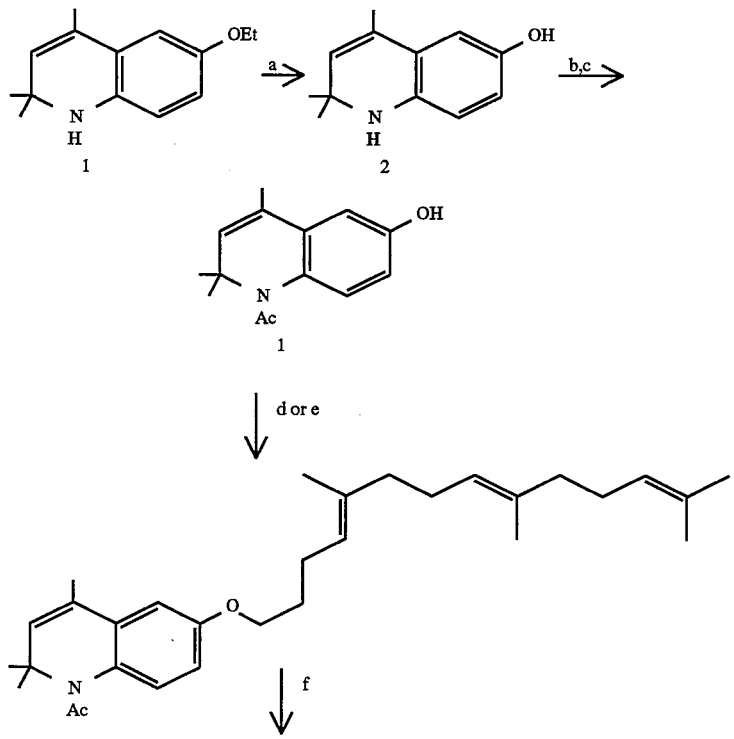

Scheme I

-continued
Scheme I

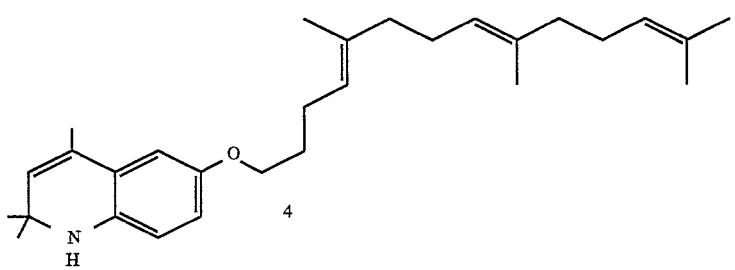

a) 48% hydrobromic acid, Δ
b) acetic anhydride, sodium acetate Δ;
c) potassium hydroxide, methanol;
d) diethylazodicarboxylate, triphenylphosphine, farnesyl ethanol, tetrahydrofuran;
e) farnesyl ethyl iodide, potassium carbonate, dimethylformamide;
f) lithium triethylborohydride, tetrahydrofuran.

The sulfide 8 was prepared as shown in scheme II. The S-aryl dimethylthiocarbamate 6 was obtained by a Newman-type rearrangement (Newman, et al., *J. Org. Chem.*, 31: 3980–84 (1966)) of O-aryl dimethylthiocarbamate 5. The reaction goes in good yield when catalyzed with p-toluenesulfonic acid under strictly oxygen-free conditions.

N-Protection is absolutely necessary in this case as the corresponding aniline-thiol is very unstable. The dimethylthiocarbamate 6 is unmasked with sodium methoxide in methanol to give thiol 7. The alkylation and deprotection were done as described in scheme I.

Scheme II

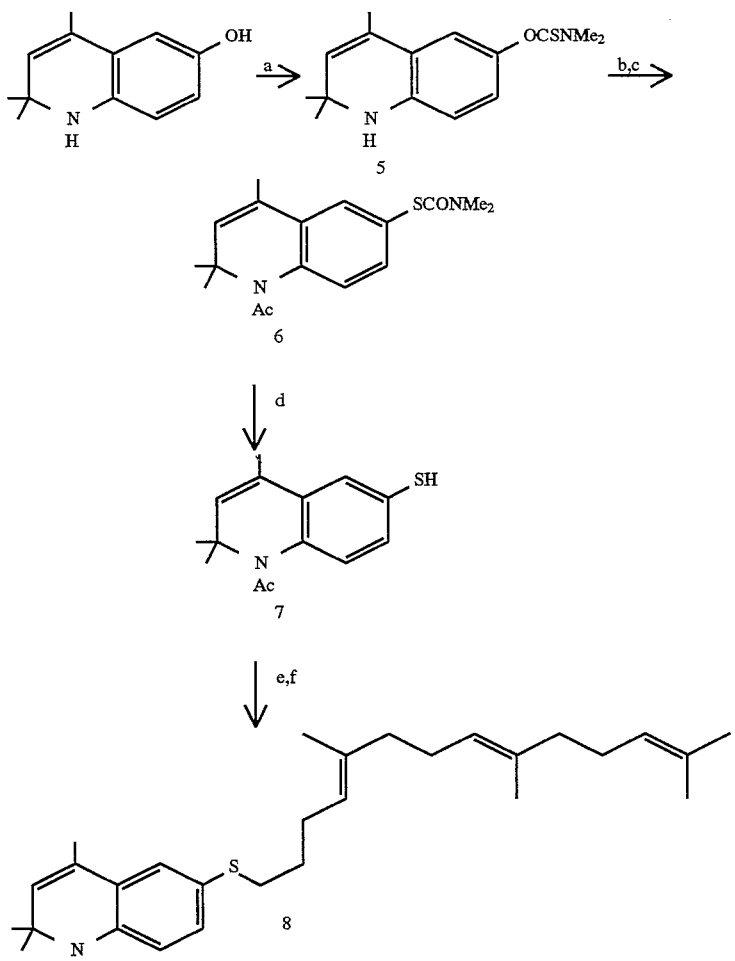

a) N,N-dimethylthiocarbamoyl chloride (Me₂NCSCl), sodium hydride, dimethylformamide, Δ;
b) p-toluenesulfonic acid, 210°, N₂;
c) acetic anhydride, sodium acetate, Δ;

-continued
Scheme II d) sodium hydroxide, methanol;
e) farnesylethyl iodide, potassium carbonate, acetonitrile;
f) lithium triethylborohydride, tetrahydrofuran.

Synthesis of the methylene-linked analogue of compound 4 can be accomplished via the sequence shown in scheme III. The dihydroquinoline is obtained from the iodine catalyzed reaction of aniline 9 and acetone following a general procedure. (*Org. Syn. Coll.*, 3: 329). The farnesylethyl side chain is attached by alkylation to the sulfone moiety. The nitrogen must be protected during this step to avoid decomposition under basic conditions. The reductive cleavage of the sulfone and super-hydride removal of the amide were smooth, and yielded compound 11 as indicated in scheme III.

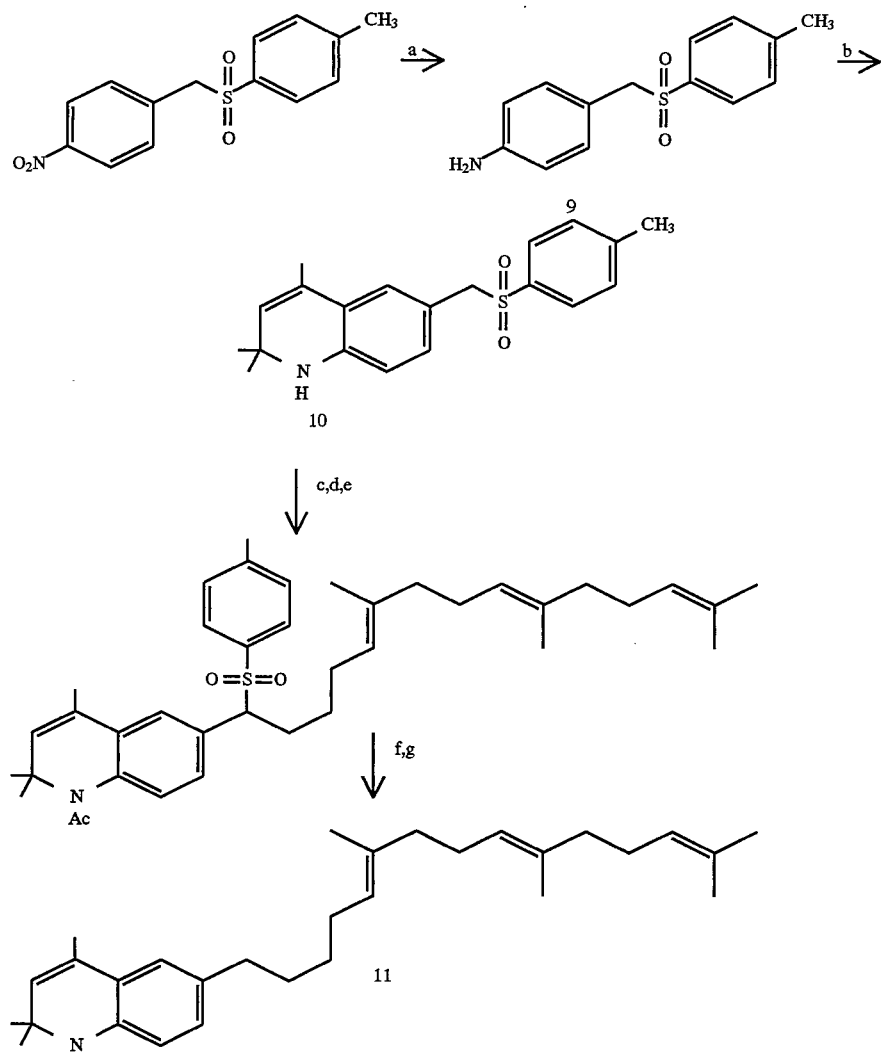

Scheme III (a) stannous chloride, ethanol, Δ;
(b) iodine, acetone, Δ;
(c) acetic anhydride, sodium acetate, acetic acid, Δ;
(d) potassium hexamethyldisilazide, tetrahydrofuran;
(e) N,N'-dimethylpropyleneurea, farnesylethyl iodide;
(f) sodium amalgam, disodium phosphate, methanol;
(g) lithium triethylborohydride, tetrahydrofuran.

The route to 1,2-dihydro-2,2,4-trimethyl-6-[[5-methyl-7-[3-(trifluoromethyl)phenyl]-4(E)hexenyl]oxy]quinoline (18) is shown in scheme IV, and follows a similar strategy as depicted in scheme III. Starting with 5-methyl-4-hexenal, (Marbet, et al., *Helv. Chim. Acta*, 50: 2095–3000 (1967)) reduction, alcohol protection, and ozonolysis proceeded smoothly to give the 4-silyloxybutanal 12. The Horner-Emmons olefination of 12 gave a 10:1 mixture of E:Z isomers, which could be chromatographically separated. The purified E-enoate 13 was reduced in a 1,2-fashion with dibal-H to give the allylic alcohol 14. The alcohol was converted into the chloride 15 and coupled with the lithium salt of sulfone 10. The toluenesulfonyl activating group was removed with sodium amalgam in buffered methanol and the crude material was then treated with fluoride to give the alcohol. The alcohol was converted into the primary iodide 17 by a standard Finklestein procedure. Coupling of iodide 17 to the N-acetyl dihydroquinoline 3 under basic catalysis followed by amide removal proceeds smoothly to give the final target compound 18.

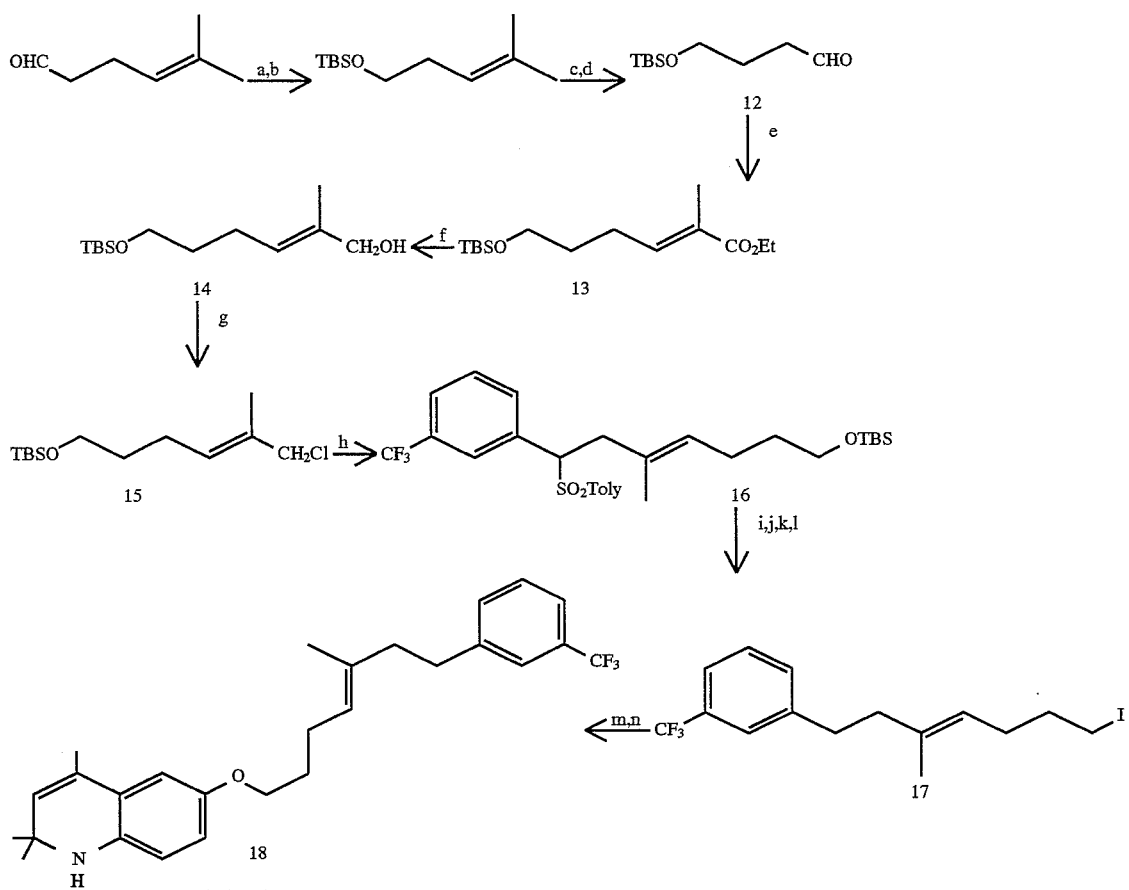

Scheme IV a) Lithium aluminum hydride, ether;
b) t-butyldimethylsilyl chloride, imidazole, dimethylformamide;
c) ozone, methanol, methylene chloride, −78°;
d) dimethyl sulfide;
e) ethyl 2-(triphenylphosphoranylidine)propionate, methylene chloride, 23°;
f) dibal-H, toluene, −78°;
g) N-chlorosuccinimide, dimethylsulfide, methylene chloride, −5°;
h) 4-methyl-1-[[[3-(trifluoromethyl)phenyl]phenyl]sulfonyl]benzene, n-butyllithium tetrahydrofuran/hexamethylphosphoramide, −5°, then chloride 15;
i) sodium amalgam, disodium phosphate, methanol;
j) tetrabutylammonium fluoride, ether;
k) methanesulfonyl chloride, triethylamine, methylene chloride, −5°;
l) sodium iodide, acetone, Δ;
m) dihydroquinoline 3, potassium carbonate, acetonitrile;
n) lithium triethylborohydride, tetrahydrofuran, 23°.

HepG2 Cell Culture Moldel

The human hepatoma HepG2 cell culture model was employed to compare the intrinsic activities of the representative compounds of the present invention relative to the tocotrienols. HepG2 cells were incubated with the indicated compounds for 4 hours at 10 µM. Cholesterol synthesis was assayed by $^{16}$C-acetate incorporation over the final hour of incubation, and HMG-CoA reductase suppression (specific activity) was assayed in the microsomal fraction isolated from parallel cultures at the end of the 4 hour incubation. Time course studies (not shown) indicated that 4 hours preincubations provided maximal suppression of sterol synthesis. The results are shown in Table I.

Table I

| Compound 10 μm | Percent of Control | |
|---|---|---|
| | Cholesterol Biosynthesis | HMGR Suppression |
| γ-Tocotrienol | 29 | 65 |
| 4 | 48 | 40 |
| 8 | 3 | N.T. |
| 11 | 89 | N.T. |
| 18 | 42 | N.T. |

N.T. = Not Tested

In Vivo Evaluation of Synthetic Analogues in Normocholesterolemic Chickens

Hypocholesterolemic activity was evaluated for representative compounds of the present invention using γ-tocotrienol as a control in normocholesterolemic chickens. Newborn male chicks (6–10 for each group) were raised on a standard corn-soybean-based control diet for two weeks and then were switched to either control or experimental diets for four weeks. Drug treatment consisted of the addition of test compound to the corn-soybean-based. At the end of the feeding period, all the birds were fasted (about 36 hours) and refed (about 48 hours) to induce cholesterolgenic enzymes prior to sacrifice. The specific activity of HMG-CoA reductase, total serum cholesterol levels, and HDL/LDL cholesterol pools were examined (Table II).

Table II

Effects of Compounds of the present invention on Lipid Parameters in Male Chickens
Orally dosed for 4-weeks at 4 mg/kg/day

| Compound | Values Given as % of Control | | | |
|---|---|---|---|---|
| | Tot.-C | LDL-C | HDL-C | HMGR |
| γ-Tocotrienol | 76.3 | 54.8 | 87.0 | N.T. |
| 4 | 65.9 | 45.3 | 89.0 | 83.8 |
| 8 | 100.9 | 99.1 | 98.2 | N.T. |
| 18 | 61.2 | 26.0 | 93.8 | 66.4 |

N.T. = Not Tested

Antioxidant Evaluation

There are a number of ways in which one can evaluate a biological antioxidant. (Halliwell, *Free Rad. Res. Comms.*, 9: 1–32 (1990)). The ability of test compounds to inhibit the oxidative modification of LDL is what is most relevant here. (Bedwell, et al., *Biochem. J.*, 262: 707–12 (1989)). The oxidative modification of LDL has been examined in vitro, using both copper and cellular (enzymatic) mediated processes. Esterbauer et al. have developed a conjugated diene assay for the measurement of LDL Oxidation. (Esterbauer, et al., *Free Rad. REs. Comms.*, 6: 67–75 (1989)). The oxidation of polyunsaturated lipids causes the conjugation of double bonds that can be quantitatively measured spectrophotometrically. The conjugated diene assay appears to be superior to older methods such as the measurement of thiobarbituric acid reactive substances (TBARS). (Yagi, *Chem. Phys. Lipids*, 45: 337–351 (1987)).

One method for the measurement of general antioxidant capacity is stopped-flow kinetic analysis. (Mukai, et al., *Bull. Chem. Soc. Jpn.*, 59: 3113–3116 (1986); Mukai, et al., *J. Org. Chem.*, 54: 557–560 (1989); Mukai, et al. *J. Org. Chem.*, 53: 430–432 (1988)). This is a sophisticated setup wherein, one measures radical transfer from a stable radical, (for example 2,6-di-tert-butyl-4-(4-methoxyphenyl) phenoxy), to a test compound spectrophotometrically as a function of time. Mukai et al. have demonstrated that a linear relationship exists between second-order rate constants derived from stopped-flow measurements and their half-peak oxidation potentials as measured voltammetrically. (Mukai, et al., *Bull. Chem. Soc. Jpn.*, 59: 3113–3116 (1986); Mukai, et al., *J. Org. Chem.*, 54: 557–560 (1989); Mukai, et al. *J. Org. Chem.*, 53: 430–432 (1988)). Voltammetry has been used by Moldeus et al. to study the antioxidant capacity of structurally related dibenzo[1,4]dichalcogenines as inhibitors of lipid peroxidation. (Cotgreave, et al., *Biochem. Pharm.*, 42: 1481–85 (1991)). In their case, a strong correlation between voltammetric potential and the ability to inhibit lipid peroxidation was observed.

As a secondary screen, test compounds are evaluated ex vivo for their oral effectiveness to inhibit LDL oxidation. In this assay, a better assessment of drug biodistribution into LDL particles is obtained. Again, the conjugated diene assay is used to assess lipid peroxidation.

Redox Potential and In Vitro LDL Oxidation

The general antioxidant capacity of several reference agents and the compounds of the present invention as measured by cyclic voltammetry is shown in Table III. A linear dependence of oxidation potentials to hydrogen atom donation capacity exists for compounds of similar structure. (Mukai, et al., *J. Org. Chem.*, 53: 430–432 (1988); Mukai, et al., *J. Org. Chem.*, 55: 552–556 (1989); Mukai, et al., *J. Org. Chem.*, 56: 4188–4192(1991)). The lower the oxidation potential (voltage) the easier the compound is to oxidize. For the in vitro LDL oxidation assay, (Steinbrecher, et al., *Proc. Natl. Acad. Sci. U.S.A.*, 81: 3883–3887 (1984)) test compounds were incubated (10 μM) with fresh plasma derived from rabbits maintained on a diet which enriches LDL in linoleate content; LDL was then isolated from the treated plasma, dialyzed, and incubated under oxidizing conditions (added $Cu^{++}$). Oxidation was measured spectrophotometrically by conjugated diene formation and the lag time extension versus control (ratio of treated/control) was determined from the first derivative of the $A_{234}$ kinetic curves.

TABLE III

Redox Potential and In Vitro LDL Oxidation

| Compound | Oxd. Potential Volts | n | LDL Oxd. Inhib. mean lag ratio |
|---|---|---|---|
| Butylatedhydroxy-toluene | N.T. | 1 | 1.38 |
| PROBUCOL | 1.12 | 28 | 1.38 |
| ETHOXYQUIN | N.T. | 1 | 1.21 |
| Ascorbate | N.T. | 1 | 1.00 |
| α-Tocopherol | 0.81 | 5 | 1.01 |
| γ-Tocopherol | N.T. | 2 | 1.17 |
| γ-Tocotrienol | 0.94 | 3 | 1.27 |
| 4 | 0.47 | 6 | 1.80 |
| 8 | 1.20 | 1 | 1.64 |

N.T. = Not Tested

Ex Vivo LDL Antioxidant Effects of Standard Reference Agents and Compounds of the Present Invention Hamsters (n=6 per group) were placed on an atherogenic diet (0.4% cholesterol+10% vitamin E stripped corn oil), and were orally dosed for 17 days with the indicated compounds at 75 mpk/day. The resistance of hamster LDL to copper-dependent oxidation in vitro was determined by conjugated dienes or lipid peroxides. (Esterbauer, et al., *Free Rad. Res. Comms.*, 6: 67–75 (1989)). Table IV gives the lag phase extension values (lag ratio) estimated from the conjugated diene curves, and the rate of initial formation of lipid hydroperoxides during LDL oxidation by $Cu^{++}$ in vitro (given as % of control at the early incubation time points).

TABLE IV

Ex Vivo LDL Lipid Peroxidation Assay

| Compound (mg/kg/d) | Conj. Dienes lag ratio (a) | % of Control 1.5 h (b) | % of Control 3.0 h (b) |
|---|---|---|---|
| Probucol (50) | 1.12 | 48 | 93 |
| α-Tocopherol (50) | >3 | 15 | 36 |
| γ-Tocotrienol (50) | 1.48 | 7 | 67 |
| Na Ascorbate (50) | 1.33 | 8 | 91 |
| 4(50) | 1.57 | 3 | 31 |
| Ethoxyquin (75) | 1.81 | 0 | 13 |

(a) Measures the ability of the antioxidant to inhibit initiation of conjugated diene formation in LDL as a function of time, expressed as treated/control.
(b) Measures the ability of the antioxidant to inhibit lipid peroxide formation in LDL at 1.5 hour and 3 hour time points.

The antioxidant effectiveness of ETHOXYQUIN and compound 4 have been examined in vitro and ex vivo [Tables III, IV]. In particular, compound 4 exhibits a lower oxidation potential and superior LDL protective capacity over standard reference agents.

The results to the above tests demonstrates that the compounds of Formula IV inhibit HMGR activity which results in a decrease in serum total cholesterol and LDL cholesterol levels, and inhibit the oxidation of LDL.

Thus, the compounds of Formula IV may be readily administered, to treat hypercholesterolemia, hyperlipidemia, and atherosclerosis, and to inhibit LDL oxidation in avian and mammalian systems in need of such treatment. For this purpose, the drug may be administered by conventional routes including, but not limited to, the alimentary canal in the form of oral doses, or by injection in sterile parenteral preparations.

In yet another aspect, the present invention provides a pharmaceutical composition which comprises a compound of Formula IV and a non-toxic pharmaceutically acceptable carrier. These carriers can be solid or liquid such as cornstarch, lactose, sucrose, olive oil or sesame oil. If a solid carrier is used, the dosage forms may be tablets, capsules, powders, troches or lozenges. If the liquid form is used, soft gelatin capsules, syrup or liquid suspensions, emulsions, or solutions in convenient dosage forms may be used. The composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiologically saline or some other sterile injectable medium immediately before use.

The dosage ranges will commonly range from about 50 mg to about 200 mg. Optimal dosages and regimes for a given host can be readily ascertained by those skilled in the art. It will, of course, be appreciated that the actual dose used will vary according to the particular composition formulated, the particular compound used, the disease being treated. Many factors that modify the action of the drug will be taken into account including age, weight, sex, diet, time of administration, route of administration, rate of excretion, condition of the patient, drug combinations, reaction sensitivities and severity of the disease.

All publications cited in this specification are indicative of the level of skill of those skilled in the art to which this invention pertains. Each publication is individually incorporated herein by reference in the location where it is cited.

The following examples are intended for illustrative purpose only and are not to be construed as limiting the invention in sphere or scope.

Melting points were recorded on a Thomas-Hoover melting point apparatus and are uncorrected. Boiling points are uncorrected. Infrared spectra were obtained on a Perkin-Elmer Model 1800 FT-IR spectrophotometer. $^1$H-NMR spectra were recorded on a Bruker AM 300 spectrometer or a Varian Gemini 300 NMR spectrometer; nuclear magnetic resonance (NMR) spectral characteristics refer to chemical shifts (δ) expressed in parts per million (ppm) with tetramethylsilane (TMS) as an internal standard. The relative area reported for the various shifts in the proton NMR spectral data corresponds to the number of hydrogen atoms of a particular functional type in the molecule. Mass spectra were measured on a Finnegan 4500 spectrometer (low resolution).

Thin-layer chromatography was performed on silica gel 60 F-254 plates purchased from E. Merck and company (visualization with iodine or phosphomolybdic acid); flash chromatography was performed on fine silica (EM Sciences, 230–240 mesh). All reactions were run under dry nitrogen unless otherwise indicated. Dry solvents were purchased from Aldrich, Milwaukee, Wisc. in sure/seal bottles and transferred by syringe under nitrogen. Most commercially available starting materials did not require further purification.

EXAMPLE 1

6-Hydroxy-1,2-Dihydro-2,2,4-Trimethylquinoline, (2)

6-Ethoxy-2,2,4-trimethyl-3,4-dihydroquinoline [Ethoxyquin (70 g, 0.32 mole)], was added to 250 mL of 48% HBr, and the mixture was heated to reflux for about 1 hour. The solution was cooled and poured into water. The aqueous suspension was made basic (pH=14) by the addition of 50% aqueous NaOH. Concentrated HCl was added to adjust the pH to about 4, then the mixture was made slightly basic by the addition of saturated sodium bicarbonate solution. The mixture was extracted with EtOAc and the organic layers were dried (brine, MgSO$_4$) and concentrated in vacuo. The thick dark oil was triturated with toluene and the insoluble residue was filtered. The crude solid was recrystallized from toluene to give the title compound as a light brown solid (mp 182°–184°, 34 g, 0.18 mole, 56%). An analytical sample was prepared by another recrystallization from toluene to provide light brown crystals, mp 182°–184°: IR (KBr) 3302, 2972, 2934, 1586, 1495, 1344, 1244, 1154, 880, 814 cm$^{-1}$; $^1$H NMR (D-6 DMSO) δ 1.12 (s, 6H), 1.33 (s, 3H), 3.34 (s, 1H), 5.17 (br s, 1H), 5.26 (s, 1H), 6.28–6.42 (m, 3H); MS m/e 190 (MH$^+$).

Anal. Calcd. for C$_{12}$H$_{15}$N$_1$O$_1$:
C, 76.16; H, 7.99; N, 7.40.
Found: C, 76.29; H, 7.95; N, 7.37.

EXAMPLE 2

1-Acetyl-6-Hydroxy-1,2-Dihydro-2,2,4-Trimethylquinoline, (3)

6-Hydroxy-1,2-dihydro-2,2,4-trimethylquinoline (12 g, 0.064 mole), and sodium acetate (10.4 g, 0.13 mole) were stirred in 75 mL of acetic anhydride at 100° for about 3 hours. The mixture was poured into water and extracted into ether. The ether extracts were combined and successively washed with water, aqueous NaHCO$_3$, dried (brine, MgSO$_4$) and concentrated in vacuo. Purification of the crude material by flash chromatography [5:1 Hexanes:Et$_2$O] yielded the diacetyl derivative as a dark yellow oil: $^1$H NMR (CDCl$_3$) δ 1.48 (s, 6H), 1.95 (s, 3H), 2.12 (s, 3H), 2.27 (s, 3H), 5.51 (s, 1H), 6.76–6.90 (m, 3H).

The diacetyl derivative (12 g) was dissolved in 100 mL of ether. The ether solution was cooled to about −78° and 1M KOH/MeOH (20 mL) was added. The reaction mixture was stirred at −78° for about 1 hour at which time TLC indicated the reaction to be complete. The solution was poured into 1N HCl and extracted into ether. The ether extracts were dried (brine, MgSO$_4$) and concentrated in vacuo. The resulting solid was recrystallized from acetonitrile to give the title compound as an off white solid (mp 214°–216°, 5.9 g, 0.026 mole, 40%): IR (KBr) 3126, 2972, 1626, 1596, 1460, 1368, 1344, 1252, 1218, 868 cm$^{-1}$; $^1$H NMR (CDCl$_3$) δ 1.20 (s, 6H), 1.70 (s, 3H), 1.80 (s, 3H), 5.23 (s, 1H), 6.34–6.44 (m, 3H), 8.61 (s, 1H); MS m/e 232 (MH$^+$).

Anal. Calcd. for $C_{14}H_{17}N_1O_2$:
C, 72.70; H, 7.41; N, 6.06.
Found: C, 72.89; H, 7.46; N, 6.09.

EXAMPLE 3

1-Acetyl-1,2-Dihydro-2,2,4-Trimethyl-6-[(5,9,13-Trimethyl-4(E),8(E),12-tetradecatrienyl)oxy]Quinoline, (Scheme I)

1-Acetyl-6-hydroxy-1,2-dihydro-2,2,4trimethylquinoline (4.0 g, 17.3 mmole), farnesyl ethanol$^{1b}$ (4.3 g, 17.3 mmole), and triphenylphosphine (5.0 g, 19.0 mmole) were dissolved in 30 mL of THF. Diethylazodicarboxylate (3.3 g, 19.0 mmole) was added dropwise over 5 minutes, and the solution was stirred at about 23° for about 40 hours. The volatile components were removed in vacuo and the oily solid was triturated with ether. The solid was removed by filtration and the residue was purified by flash chromatography [gradient 6:1 to 5:1 Hexanes:Ether] to yield the title compound as a yellow oil (6.1 g, 13.2 mmole, 76%): IR (film) 2924, 1672, 1606, 1492, 1364, 1324, 1204 cm$^{-1}$; $^1$H NMR (CDCl$_3$) δ 1.50 (s, 6H), 1.59 (s, 6H), 1.61 (s, 3H), 1.68 (s, 3H), 1.83 (m, 2H), 1.94–2.14 (m, 8H), 2.01 (s, 3H), 2.11 (s, 3H), 2.17 (m, 2H), 3.95 (t, J=6.4 Hz, 2H), 5.08–5.19 (m, 3H), 5.54 (s, 1H), 6.65–6.79 (m, 3H); MS m/e 464 (MH$^+$).

Anal. Calcd. for $C_{31}H_{45}N_1O_2$:
C, 80.30; H, 9.78; N, 3.02.
Found: C, 80.03; H, 9.70; N, 3.04.

EXAMPLE 4

1,2-Dihydro-2,2,4-Trimethyl-6-[(5,9,13-Trimethyl-4(E), 8(E), 12-tetradecatrienyl)oxy]Quinoline, (4)

about 23° for about 60 hours, the reaction was quenched by the careful addition of saturated NH4Cl solution. The mixture was poured into water and extracted into ether. The ether extracts were dried (brine, MgSO$_4$) and concentrated in vacuo. Purification of the crude material by flash chromatography [20:1 Hexanes:Et$_2$O] yielded the dihydroquinoline as a yellow oil (6.2 g, 12. 8 mmole, 72%): IR (film) 3364, 2964, 1650, 1580, 1498, 1446, 1380, 1260, 1156 cm$^{-1}$; $^1$H NMR (CDCl$_3$+TFA) δ 1.50 (s, 6H), 1.57 (s, 6H), 1.59 (s, 3H), 1.65 (s, 3H), 1.85 (m, 2H), 1.94–2.14 (m, 8H), 2.07 (s, 3H), 2.16 (m, 2H), 3.94 (t, J=6.3 Hz, 2H), 5.0 (m,3H), 5.63 (s, 1H), 6.76 (d of d, J=2.5, 8.6 Hz, 1H), 6.88 (d, J=2.5 Hz, 1H), 7.32 (d, J=8.6 Hz, 1H); MS m/e 422 (MH$^+$).

Anal. Calcd. for $C_{29}H_{43}N_1O_1$:
C, 82.61; H, 10.28; N, 3.32.
Found: C, 82.71; H, 10.40; N, 3.21.

EXAMPLE 5

O-[1,2-Dihydro-2,2,4-Trimethylguinoline] Dimethylthiocarbamate, (5)

6-Hydroxy-1,2-dihydro-2,2,4-trimethylquinoline (6 g, 31.7 mmole) and dimethylthiocarbamoyl chloride (5.2 g, 42.3 mmole) were dissolved in 50 mL of DMF. The mixture was cooled to about 0° and sodium hydride (1.3 g, 31.7 mmole, 60%) was added portionwise. The mixture was warmed to about 60° until complete by TLC (1 hour). The solution was poured into water and the solid was collected by filtration to yield the title compound as brown solid (mp 125–128, 8.0 g, 29 mmole, 92%). A portion of the material was recrystallized from toluene/hexanes for analysis (pale amber crystals, mp 128°–130°): IR (KBr) 3322,2962, 1536, 1496, 1482, 1394, 1288, 1254, 1194, 1154, 880, 814 cm$^{-1}$; $^1$H NMR (CDCl$_3$) δ 1.25 (s, 6H), 1.92 (s, 3H), 3.29 (s, 3H), 3.43 (s, 3H), 5.29 (s, 1H), 6.37 (d, J=8.2 Hz, 1H), 6.65 (d of d, J=8.2,2.6 Hz, 1H), 6.70 (d, J=2.6 Hz, 1H); MS m/e 277 (MH$^+$).

Anal. Calcd. for $C_{15}H_{20}N_2O_1S_1$:
C, 65.18; H, 7.29; N, 10.14.
Found: C, 65.53; H, 7.36; N, 9.82.

EXAMPLE 6

S-[1,2-Dihydro-2,2,4-Trimethylquinoline] Dimethylthiocarbamate, (Scheme II)

p-Toluenesulfonic acid monohydrate (550 mg, 2.9 mmole) was heated under vacuum (15 mm) for about 3

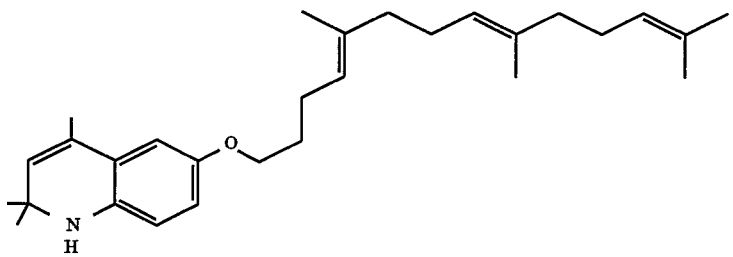

1-Acetyl-1,2-dihydro-2,2,4-trimethyl-6-[(5,9,13-trimethyl-4(E), 8(E), 12-tetradecatrienyl) oxy]quinoline (8.2 g, 17.7 mmole) was dissolved in 75 mL of THF and the solution was cooled to about −10°. Lithium triethylborohydride (1.0M, 89 mL, 89 mmole) was added dropwise to the mixture end the cooling bath was removed. After stirring at hours at about 150° to remove water. O-[1,2-Dihydro-2,2, 4-trimethylquinoline] dimethylthiocarbamate 5 (4 g, 14.5 mmole) was added to the cooled acid, and the mixture was slowly heated under 15 mm of pressure to 180°–200° at which time the components became a homogeneous melt. The vessel was pressurized with nitrogen (1 atm). The mixture was then heated at about 207° for about 1 hour, at which time TLC indicated the conversion to be approximately 75% complete. The reaction mixture was cooled and dissolved into ethyl acetate. The solution was treated with activated carbon, filtered and concentrated in vacuo. Purification of the crude material by flash chromatography [gradient 4:1 to 2:1 Hexanes:Et$_2$O] yielded the dihydroquinoline as an amber solid (2.4 g, 8.7 mmole, 60%). A sample was recrystallized from toluene/hexanes for analysis (pale amber crystals, mp 89°–90°): IR (KBr) 3332,2970, 1651, 1596, 1488, 1448, 1362, 1260, 1102, 1092, 828 cm$^{-1}$; $^1$H NMR (CDCl$_3$) δ 1.27 (s, 6H), 1.96 (s, 3H), 3.04 (br s, 6H), 5.31 (s, 1H), 6.56 (d, J=1.7 Hz, 1H), 6.72 (d of d, J=9.0, 1.7 Hz, 1H), 6.7.03 (d, J=9.0 Hz, 1H); MS m/e 277 (MH$^+$).

Anal. Calcd. for C$_{15}$H$_{20}$N$_2$O$_1$S$_1$:
C, 65.18; H, 7.29; N, 10.14.
Found: C, 65.33; H, 7.23; N, 10.04.

EXAMPLE 7

1-Acetyl-S-[1,2-Dihydro-2,2,4-Trimethylquinoline]

S-[1,2-Dihydro-2,2,4-trimethylquinoline] dimethylthiocarbamate (6.5 g, 23.6 mmole) and sodium acetate (3.9 g, 47.1 mmole) were stirred in 50 mL of acetic anhydride at reflux for about 3 hours. The mixture was slowly poured into excess saturated NaHCO$_3$ solution (caution!). The mixture was extracted into ethyl acetate, and the organic layers were dried (brine, MgSO$_4$) and concentrated in vacuo. Purification of the crude solid by recrystallization from toluene/hexanes provided the N-acetyl derivative as a pale amber solid, mp 110°–112° (2.2 g, 6.9 mmole, 29%): IR (KBr) 2960, 1683, 1651, 1552, 1492, 1474, 1366, 1314, 1242, 1098, 840 cm$^{-1}$; $^1$H NMR (CDCl$_3$) δ 1.48 (s, 6H), 1.97 (s, 3H), 2.18 (s, 3H), 2.99 (br s, 6H), 5.49 (s, 1H), 6.92 (d, J=1.2 Hz, 1H), 7.16 (m, 2H); MS m/e 319 (MH$^+$).

Anal. Calcd. for C$_{17}$H$_{22}$N$_2$O$_2$S$_1$:
C, 64 . 12; H, 6.96; N, 8.80.
Found: C, 64.19; H, 6.82; N, 8.76.

EXAMPLE 8

1-Acetyl-1,2-Dihydro-2,2,4-Trimethylguinoline-6-Thiol, (7)

1-Acetyl-S-[1,2-dihydro-2,2,4-trimethylquinoline] dissolved in a solution of sodium methoxide prepared from sodium (360 mg, 15.7 mmole) in methanol (20 mL). The mixture was stirred for about 48 hours at about 23° at which time TLC indicated complete hydrolysis. The mixture was poured into 1N HCl and extracted into ether. The ether extracts were combined, dried (brine, MgSO$_4$) and concentrated in vacuo. Purification of the crude material by flash chromatography [gradient 5:1 to 4:1 Hexanes:Et$_2$O] yielded the free thiophenol as a yellow oil (1.4 g, 5.7 mmole, 72%):

$^1$H NMR (CDCl$_3$) δ 1.48 (s, 6H), 1.96 (s, 3H), 2.16 (s, 3H), 5.45 (s, 1H), 6.73 (d, J=1.2 Hz, 1H), 6.98 (d of d, J=1.2, 9.0 Hz, 1H), 7.06 (d, J=9.0 Hz, 1H), MS m/e 248 (MH$^+$).

EXAMPLE 9

1-Acetyl-1,2-Dihydro-2,2,4-Trimethyl-6-[(5,9,13-Trimethyl-4(E),8(E),12tetradecatrienyl)thio]

1-Acetyl-1,2-dihydro-2,2,4-trimethylquinoline-6thiol (1.4 g, 5.67 mmole), potassium carbonate (1.2 g, 8.5 mmole), and farnesylethyl iodide (2.0 g, 5.67 mmole) were added to 30 mL of acetonitrile. TLC indicated the reaction to be complete after stirring for about 30 minutes at about 23°. The mixture was poured into water and extracted into ether. The ether extracts were combined, dried (brine, MgSO$_4$) and concentrated in vacuo. Purification of the crude material by flash chromatography [15:1 Hexanes:Et$_2$O] yielded the title compound as a yellow oil (2.2 g, 4.59 mmole, 81%). A small sample was distilled in a Kugelrohr oven (bath 180°–190°/0.15 mm) for analysis: IR (film) 2924, 1680, 1594, 1492, 1362, 1314 cm$^{-1}$; $^1$H NMR (CDCl$_3$) δ 1.48 (s, 6H), 1.56 (s, 6H), 1.58 (s, 3H), 1.64 (s, 3H), 1.65 (m, 2H), 1.90–2.15 (m, 10H), 1.98 (s, 3H), 2.14 (s, 3H), 2.86 (t, J=7.1 Hz, 2H), 5.07 (m,3H), 5.45 (s, 1H), 6.75 (d, J=1.7 Hz, 1H), 7.02 (d of d, J=1.7, 11 Hz, 1H), 7.06 (d, J=11.0 Hz, 1H); MS m/e 480 (MH$^+$).

Anal. Calcd. for C$_{31}$H$_{45}$N$_1$O$_1$S$_1$:
C, 77.61; H, 9.45; N, 2.92.
Found: C, 77.31; H, 9.38; N, 2.88.

EXAMPLE 10

1,2-Dihydro-2,2,4-Trimethyl-6-[(5,9,13-Trimethyl-4(E),8(E),1 2-tetradecatrienyl)thio]Quinoline, (8)

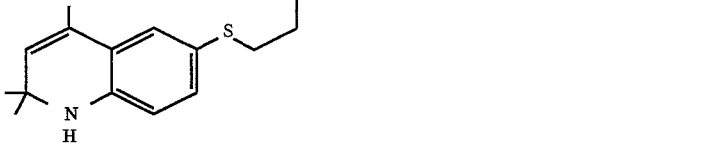

1-Acetyl-1,2-dihydro-2,2,4-trimethyl-6-[(5,9,13-trimethyl-4 (E), 8 (E), 12-tetradecatrienyl)thio]quinoline (1.9 g, 3.97 mmole) was dissolved in 20 mL of THF and the solution was cooled to about −10°. Lithium triethylborohydride (1.0M, 19.8 mL, 19.8 mmole) was added dropwise to the mixture and the cooling bath was removed. After stirring at about 23° for about 15 hours, the reaction was quenched by the careful addition of saturated NH$_4$Cl solution. The mixture was poured into water and extracted into ether. The ether extracts were dried (brine, MgSO$_4$) and concentrated in vacuo. Purification of the crude material by flash chromatography [20:1 Hexanes:Et$_2$O]yielded the dihydroquinoline as a yellow oil (1.3 g, 2.97 mmole, 75%): IR (film) 3372,2964, 1652, 1598, 1448, 1258, 1168 cm$^{-1}$; $^1$H NMR (CDCl$_3$) δ 1.26 (s, 6H), 1.59 (s, 9H), 1.65 (m, 2H), 1.67 (s, 3H), 1.95 (s, 3H), 1.95–2.15 (m, 10H), 2.16 (m, 2H), 2.86 (t, J=7.2 Hz, 2H), 3.72 (br s, 1H), 5.08 (m,3H), 5.26 (s, 1H), 6.40 (d, J=1.8 Hz, 1H), 6 of d, J=8.0, 1.8 Hz, 1H), 6.94 (d, J=8.0 Hz, 1H); MS m/e 438 (MH$^+$).

Anal. Calcd. for $C_{29}H_{43}N_1S_1$:
C, 79.57; H, 9.90; N, 3.20.
Found: C, 79.61; H, 9.61; N, 3.24.

EXAMPLE 11

4-Methyl-1-[[[4-Nitrophenyl]methyl]sulfonyl] benzene, (Scheme III)

4-Nitrobenzyl chloride (5.0 g, 29.1 mmole) and sodium p-toluenesulfinate (6.8 g, 37.9 mmole) were dissolved in 50 mL of dry DMF. The mixture was stirred at about 23° for about 18 hours then diluted with water. The sulfone crystallized from the aqueous mixture and was filtered. The sulfone was purified by recrystallization from ethanol to give a pale yellow crystalline solid, mp 188°–190° (7.6 g, 25.9 mmole, 89%): IR (KBr) 2994, 1598, 1514, 1490, 1342, 1312, 1304, 1148, 824 cm$^{-1}$; $^1$H NMR (CDCl$_3$) δ 2.44 (s, 3H), 4.38 (s, 2H), 7.27 (m, 4H), 7.53 (d, J=8.3 Hz, 2H), 8.13 (d, J=8.3 Hz, 2H); MS m/e 292 (MH$^+$).

Anal. Calcd. for $C_{14}H_{13}N_1O_4S_1$:
C, 57.72; H, 4.50; N, 4.81.
Found: C, 57.72; H, 4.46; N, 4.80.

EXAMPLE 12

4-[[[(4-Methylphenyl)sulfonyl]methyl]Aniline, (9)

A solution of 4-methyl-1-[[[4-nitrophenyl]methyl]sulfonyl] benzene (15 g, 51 mmol) in ethanol (250 mL) containing stannous chloride dihydrate (57.5 g, 255 mmol) was heated to reflux for about 3 hours. The mixture was cooled, poured into water and neutralized with 20% aqueous sodium hydroxide. The solution was filtered and dried under aspirator vacuum. The pale yellow solid was washed with hot ethyl acetate (3 L) and the solvent removed in vacuo to give 3 as white needles (13.4 g, 5.1 mmole, 75%) mp 217°–218°: IR (KBr) 3444, 3370, 1636, 1612, 1294, 1284, 1142 cm$^{-1}$; $^1$H NMR (CDCl$_3$) δ 2.40 (s, 3H), 3.70 (s, exchanges with D$_2$O, 2H), 4.16 (s, 2H), 6.54 (d, J=8.5 Hz, 2H), 6.83 (d, J=8.5 Hz, 2H), 7.22 (d, J=6.4 Hz, 2H), 7.50 (d, J=6.4,2H); MS m/e 261 (M$^+$).

Anal. Calcd. for $C_{14}H_{15}N_1O_2S_1$:
C, 64.34; H, 5.78; N, 5.36.
Found: C, 64.50; H, 5.79; N, 5.32.

EXAMPLE 13

1,2-Dihydro-2,2,4-Trimethyl-6-[1-(4Methylphenyl) sulfonyl]Quinoline, (10)

A solution of 4-[[(4methylphenyl)sulfonyl]methyl] aniline (3.1 g, 10.6 mmol) in dioxane (150 mL) containing I$_2$ (160 mg, 0.6 mmol) was heated to about 90° C. and acetone(250 mL) was added dropwise such that a distillation rate of 1–2 drops/sec is maintained. After about 6 hours, acetone (100 mL) was added and the reaction mixture was refluxed overnight. The above sequence was repeated over a 12 hour period. The reaction mixture was cooled, concentrated and the black viscous oil was purified by flash chromatography with 30% ethyl acetate in hexanes as eluant to give the title compound as a pale yellow solid (2.17 g , 6.4 mmole, 52%) which can be further purified by recrystallization from ethyl acetate-ether to give a white solid mp 134°–135°: IR (KBr) 3380, 1375, 1300, 1140, 815 cm$^-$; $^1$H NMR (CDCl$_3$) δ 1.24 (s, 6H), 1.77 (s, 3H), 2.39 (s, 3H), 3.77 (s, exchanges with D$_2$O, 1H), 4.13 (s, 2H), 5.26 (s, 1H), 6.30 (d, J=8.0 Hz, 1H) 6.57 (s, 1H), 6.69 (dd, J=1.8, 6.3 Hz, 1H), 7.23 (d, J=8.3 Hz, 2H), 7.52 (d, J=8.3 Hz, 2H); MS m/e 341 (M$^+$).

Anal. Calcd for $C_{20}H_{23}N_1O_2S_1$:
C, 70.35; H, 6.79; N, 4.10.
Found: C, 70.37; H, 6.81; N, 4.04.

EXAMPLE 14

N-Acetyl-1,2-Dihydro-2,2,4-Trimethyl-6-[1-(4methylphenyl)sulfonyl]Quinoline, (Scheme III)

A solution of 1,2-dihydro-2,2,4-trimethyl-6-[1(4-methylphenyl)sulfonyl]quinoline (3.4 g, 10 mmol) in acetic anhydride (9.6 mL, 100 mmol) containing sodium acetate (0.9 g, 11 mmol) was heated to reflux for about 1 hour, then stirred overnight at about 23°. The reaction is not complete as indicated by TLC analysis. Additional acetic anhydride (5 mL) was added and the mixture was heated to reflux for about 2 hours then cooled. The reaction mixture was poured into dilute sodium hydroxide (10%) and the aqueous layer extracted with ether. The ether extracts were dried (brine, MgSO$_4$) and concentrated in vacuo. The residue was purified by flash chromatography using 50% ethyl acetate in hexanes as an eluant to give N-acetyl derivative (3.19 g, 8.3 mmole, 83%) as a yellow oil: IR (film) 3018,2972,2926, 1675, 1315, 1150, 825 cm$^{-1}$; $^1$H NMR (CDCl$_3$) δ 1.48 (s,6H), 1.86 (s, 3H), 2.11 (s, 3H), 2.40 (s, 3H), 4.24 (s, 2H), 5.48(s, 1H), 6.70–6.67(m, 1H), 6.85–6.81(m, 2H), 7.49(d, J=8.4 Hz, 2H), 7.51(d, J=8.4 Hz, 2H); MS m/e 383 (M$^+$).

EXAMPLE 15

N-Acetyl-1,2-Dihydro-2,2,4-Trimethyl-6-[1-f(4-Methylphenyl) sulfonyl)-6,10,14-Trimethyl-5 (E), 9 (E), 13Pentadecatrienyl] Quinoline, (Scheme III)

A solution of N-acetyl-1,2-dihydro-2,2,4-trimethyl-6-[1-(4-methylphenyl)sulfonyl]quinoline (7.89 g, 23.1 mmol) in THF (100 mL) was cooled to −78°, and treated with potassium bis(trimethylsilyl)amide (46.2 mmol, 23.1 mmol, 0.5 M in toluene) and stirred for about 15 minutes. DMPU (26 mL) was added to the reaction mixture followed by a solution of farnesylethyl iodide (8.2 g, 23.1 mmol) in THF (25 mL). The reaction mixture was stirred for about 1 hour at about −78° then poured into water (100 mL), and the aqueous layer was extracted with ether. The organic extracts were combined, dried (brine, MgSO$_4$) and concentrated in vacuo. The residue was purified by flash chromatography using 20% ethyl acetate in hexanes as an eluant to give the alkylated sulfone as a yellow oil (8.13 g, 13.2 mmoles, 57%): IR (film) 2926, 1675, 1320, 1150, 820 cm$^{-1}$; $^1$H NMR (CDCl$_3$) δ 1.34–1.22 (m, 4H), 1.48 (s, 6H), 1.52 (s, 3H), 1.55 (s, 3H), 1.57 (s, 3H), 1.68 (s, 3H), 1.81 (s, 3H), 1.93–2.10 (m, 10H), 2.10 (s, 3H), 2.35 (s, 3H), 3.98 (dd, J=3.9, 11.5 Hz, 1H), 4.98–5.07 (m, 3H), 5.47 (s, 1H), 6.92 (d, J=8.2 Hz, 1H), 7.02–7.05 (m, 2H), 7.14 (d J=8.11 Hz, 2H), 7.38 (d, J =8.1 Hz, 2H); MS m/e 615 (M$^+$).

Anal. Calcd for $C_{39}H_{53}N_1O_3S_1$:
C, 76.05; H, 8.67; N, 2.28.
Found: C, 76.15; H, 8.68; N, 2.30.

EXAMPLE 16

N-Acetyl-1,2-Dihydro-2,2,4-Trimethyl-6-[6,10,14-Trimethyl-5(E),9(E),13-Pentadecatrienyl]Quinoline, (Scheme III)

A mixture of N-acetyl-1,2-dihydro-2,2,4-trimethyl-6-[1-(4-methylphenyl)sulfonyl)-6,10,14-trimethyl-5 (E), 9(E), 13-pentadecatrienyl]quinoline (8.1 g, 13.2 mmol) and disodium hydrogen phosphate (7.5 g, 53 mmol) in methanol (50 mL) were cooled to about 0°. Sodium amalgam (10 mesh, 6% Na, 18.6 g) was added, and after about 30 minutes, the reaction mixture was warmed to 23° C. and stirred for an additional 12 hours. The reaction mixture was poured into water (50 mL) and the aqueous layer extracted with ether. The ether extracts were combined, dried (brine, MgSO$_4$) and concentrated in vacuo. The residue was purified by flash chromatography [gradient 10:1 to 5:1 Hexanes:EtOAc] to give the N-acetyl derivative as a clear oil (3.48 g, 7.5 mmole, 57%): IR (film) 2965–2854, 1678, 1450, 823 cm$^{-1}$; $^1$H NMR (CDCl$_3$) δ 1.28–1.41 (m, 2H), 1.44 (s, 6H), 1.53 (s, 12H), 1.61 (s, 3H), 1.84–1.97 (m, 12H), 2.08 (s, 3H), 2.54 (t, J=7.6 Hz, 2H), 4.99–5.09 (m, 3H), 5.43 (s, 1H), 6.69 (d, J=8.0 Hz, 1H), 6.92 (d, J=8.0 Hz, 1H) 6.94 (s, 1H); MS m/e 461 (M$^+$).

Anal. Calcd for C$_{32}$H$_{47}$N$_1$O$_1$:

C, 83.24; H, 10.26; N, 3.03.

Found: C, 83.64; H, 10.40; N, 3.05.

EXAMPLE 17

1,2-Dihydro-2,2,4-Trimethyl-6-[6,10,14-Trimethyl5 (E),9(E), 13-Pentadecatrienyl]Quinoline, (11)

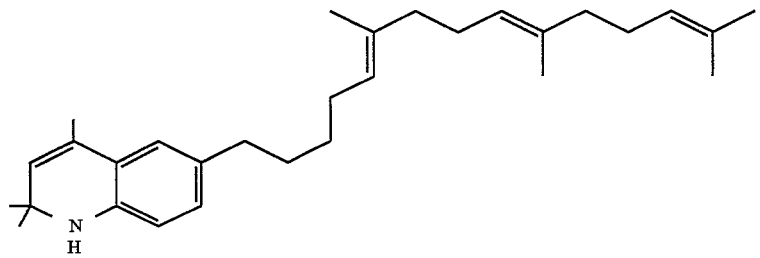

Lithium triethylborohydride (22.7 mL, 22.7 mmol, 1.0 M in THF) was added to a solution of the acetamide (3.48 g, 7.56 mmol) maintained at about 0° in THF (50 mL). The reaction was slowly warmed to about 23° and stirred for about 12 hours. The reaction mixture was poured into water (100 mL) and the aqueous layer extracted with ethyl acetate. The organic extracts were combined, dried (brine, MgSO$_4$) and concentrated in vacuo. The residue was purified by flash chromatography [20:1 Hexanes: EtOAc] to give in order of elution: Compound of example (11)(1.28 g, 3.1 mmole, 40%) and the starting material (1.42 g, 3.1 mmole, 41%): IR (film) 3380,2900, 1450, 1380, 810 cm$^{-1}$; $^1$H NMR (CDCl$_3$) δ 1.25 (s, 6H), 1 17–1 42 (m, 4 H), 1.42–1.59 (m, 12H), 1.68 (s, 3H), 1.98 (s, 6 H), 1.96–2.04 (m, 4 H), 2.34 (m, J=7.2 Hz, 2H), 3.54 (br s, exchanges with D$_2$0, 1H), 5.07–5.12 (m, 3H), 5.29 (s, 1H), 6.36 (d, J=7.8 Hz, 1H), 6.86 (d, J=7.9 Hz, 1H), 6.86 (s, 1H); MS m/e 419 (M$^+$).

Anal. Calcd for C$_{30}$H$_{45}$N$_1$:

C, 85.86; H, 10.81; N, 3.34.

Found: C, 85.87; H, 10.82; N, 3.23.

EXAMPLE 18

[4-(1,1-dimethylethyl)dimethylsilyloxy]butana], C12) and ethyl 2-methyl-6-[(1,1-dimethylethyl) dimethylsilyloxy]-2(E)-hexenoate, (13)

To a solution of 5-methyl-4-hexenal (Marbet, et al., Helv. Chim. Acta., 50: 2095–3000 (1967)) (18.8 g, 168 mmol) in ethanol (100 mL) at 0° is added dropwise a solution of sodium borohydride (1.7 g, 46.2 mmol) in methanol (100 mL). The reduction is complete in about 30 minutes as indicated by TLC analysis. The reaction mixture is neutralized with diluted aqueous acetic acid (10%), then poured into water and the aqueous layer extracted with ether. The ether extracts are washed with water, dried (brine, MgSO$_4$) and concentrated to give the alcohol (13.89 g, 122 mmol, 57%) as a clear oil (bp 108°–120°/0.25 mm Hg).

A solution of alcohol (13.9 g, 122 mmol) in DMF (100 mL), tert-butyldimethylsilyl chloride (20.1g, 134 mmol) and imidazole (9.95g, 146 mmol) is stirred at about 23° for about 24 hour. The reaction mixture is poured into water and the aqueous layer extracted with ether. The ether extracts are washed with water, dried (brine, MgSO$_4$) and concentrated. The residue is purified by flash chromatography using hexanes as eluant to give the silyl ether (17.9 g, 64%, 78.5 mmol) as a clear oil (bp 57°–60° C./0.25 mmHg): IR(film) 2956,2930,2888, 1380, 1250, 1100, 840 cm$^{-1}$; $^1$H NMR (CDCl$_3$) δ 0.042 (s, 6H), 0.89 (s, 9H), 1.54 (d of t, J=8.17, 7.0 Hz,2H), 1.59 (s, 3H), 1.67 (s, 3H), 2.02 (dd, J=7.3, 14.8 Hz, 2H), 3.59 (t, J=6.5 Hz, 2H), 5.11 (t, J=7.2 Hz, 1H); MS 228 (M$^+$).

Anal. Calcd. for C$_{13}$H$_{28}$OSi:

C, 68.35; H, 12.35.

Found: C, 68.66; H, 12.50.

A solution of the silyloxyolefin (2.0 g, 8.8 mmol) in dichloromethane (50 mL) is cooled to about –78° and ozone is bubbled through the solution until a light blue color remains. The ozone flow is turned off and nitrogen is bubbled through the solution until the ozone color fades. Dimethyl sulfide (1.9 mL, 36.4 mmol) is added and the mixture stirred at about –78° for about 1 hour and at about 23° for about 2 hours. (Note: The aldehyde 12 decomposed during an attempted distillation thus the aldehyde was not isolated.) To the reaction mixture is added (carbethoxyethylidene) triphenylphosphorane (3.3 g, 8.8 mmol) and the yellow solution is stirred for about 2 hours. Although the yellow color of the phosphorane is gone after about 2 hours, TLC analysis indicates some aldehyde remains. Additional phosphorane (0.5 g, 1.4 mmol) is added and the reaction mixture is stirred for about 48 hours at about 23°. The reaction mixture is concentrated, triturated with pentane, filtered, concentrated and the residue purified by flash chromatography to give 13 (2.3295 g, 93%, 8 1 mmol) as a clear oil: IR (film) 1710, 1370, 1260, 1100, 840 cm$^{-1}$; $^1$H NMR (CDCl$_3$) δ 0.023 (s, 6H), 0.87 (s, 9H), 1.26 (t, J=7.1 Hz, 3H), 1.62(dt, J=14.6, 6.2 Hz, 2H), 1.80 (s, 3H), 2.22 (q, J=7.4, 14.9 Hz, 2H), 3.60 (t, J=6.2 Hz, 2H), 4.15 (q, J=7.1, 14.2 Hz, 2H), 6.74 (t, J=7.5 Hz, 1H); MS 286 (M$^+$).

Anal. Calcd. for $C_{15}H_{30}O_3Si$
C, 62.89; H, 10.56.
Found: C, 62.88; H, 10.65.

EXAMPLE 19

2-Methyl-6-[(1,1-dimethylethyl) dimethylsilyloxy]-2(E)-hexenol, (14)

Diisobutylaluminum hydride (42 mL, 42 mmol, 1.0 M in toluene) in THF (50 mL) is added to a solution of ester 13 (6.0 g, 21.0 mmol) in THF (50 mL) at about −78° and stirred for about 4 hours. A solution of NaOH (1N, 100 mL) is added and the aqueous layer extracted with ether. The ether extracts are combined, washed with saturated aqueous sodium chloride, dried over magnesium sulfate and concentrated. The oily residue is purified by flash chromatography to give in order of elution (0.12 g, 0.49 mmol, 2%) of the Z isomer and 14 (3.677 g, 15.1 mmol, 72%) of a mixture of E and Z isomers (E/Z=30.6/1): IR(film) 3335,2900, 1450, 1390, 1360, 1250, 1100, 1060, 840 cm$^{-1}$; $^1$H NMR (CDCl$_3$) δ 0.014 (s, 6H), 0.85 (s, 9H), 1.21 (s, 1H, exchanges with D$_2$O), 1.53 (dt, J=14.9, 6.4 Hz, 2H), 1.62 (s, 3H), 2.04 (dd, J =7.1, 14.8 Hz, 2H), 3.56 (t, J=6.4 Hz, 2H), 3.95 (s, 2H), 5.37 (tq, J=1.4, 7.3 Hz, 1H); MS m/e 244 (M$^+$).

Anal. Calcd. for $C_{13}H_{20}O_2Si$
C, 63 . 88; H, 11.55.
Found: C, 64.00; H, 11.54.

EXAMPLE 20

6-Chloro-1-[(1,1-dimethylethyl)dimethylsilyloxy]-5-methyl-4(E)-hexene, (15)

N-chlorosuccinimide (2.5 g, 18.7 mmol) is dissolved in dichloromethane (100 mL), cooled to about 0° and treated with dimethyl sulfide (1.4 mL, 19.5 mmol) and stirred for about 1 hour. The alcohol (3.3 g, 13.5 mmol) is added and the reaction mixture stirred for about 3 hours. The solvent is removed in vacuo and the residue purified by flash chromatography with 10% ethyl acetate in hexanes as eluant. The chloride 15 is isolated as a clear oil (2.9 g, 11.1 mmol, 82%).

EXAMPLE 21

General Procedure for the Synthesis of Benzyl Sulfones

The commercially available benzyl bromide or benzyl chloride (50 mmole) and sodium p-toluenesulfinate (65 mmole) were dissolved in 50–100 mL of dry DMF. The mixtures were stirred at about 23° for about 18 hours then diluted with water. In most cases the sulfones crystallized from the aqueous mixture and were filtered, if not, they were extracted into ether. The compounds were purified by recrystallization (EtOH) or column chromatography.

4-Methyl-1-[[[3-(trifluoromethyl) phenyl]methyl] sulfonyl]benzene

Colorless plates, mp 139°–140°: IR (KBr) 2954, 1614, 1598, 1450, 1332, 1312, 1288, 1164, 1142, 1116, 1074 cm$^{-1}$; $^1$H NMR (CDCl$_3$) δ 2.44 (s, 3H), 4.34 (s, 2H), 7.16 (s, 1H), 7.26 (d, J=8.1 Hz, 2H), 7.42 (m, 1H), 7.50 (d, J=8.1 Hz, 2H), 7.58 (d, J=7.5 Hz, 1H); MS m/e 315 (MH$^+$).

Anal. Calcd. for $C_{15}H_{13}F_3O_2S_1$:
C, 57.32; H, 4.17.
Found: C, 57.28; H, 4.08.

EXAMPLE 22

7-[(1,1-Dimethylethyl)dimethylsilyloxy]-3-Methyl-1-[(4-Methylphenyl) sulfonyl]-1-[3(Trifluoromethyl) phenyl]-hept-3(E)-ene , (16)

4-Methyl-1-[[[3-(trifluoromethyl)phenyl]methyl] sulfonyl]benzene (2.8 g, 8.9 mmol) in THF (20 mL) is cooled to about −78°, treated with nBuLi (8.9 mL, 8.95 mmol) and stirred for about 1 hour. Dry DMPU (5 mL) is added followed by a solution of the allylic chloride 15 (1.96 g, 7.48 mmol) in THF (10 mL). The mixture is warmed to about 0° and stored for about 48 hours. The reaction is poured into water (50 mL) and extracted with ether. The ether extracts are dried (MgSO$_4$) and concentrated. The residue is purified by flash chromatography with 10% ethyl acetate in hexanes as eluant to give 16 (2.60 g, 4.81 mmol, 65%) as a white solid (mp 80°–85°): IR (KBr) 1330, 1300, 1160, 1140, 1125, 1100, 840, 775 cm$^{-1}$; $^1$H NMR (CDCl$_3$) δ 0.06 (s, 6H), 0.80 (s, 9H), 1.14–1.31 (m, 2H), 1.44 (s, 3H), 1.80 (dd, J=14.6, 7.3 Hz, 2H), 2.35 (s, 3H), 2.78 (dd, J=12.2, 13.8 Hz, 1H), 3.05 (d, J=13.9 Hz, 1H), 3.10–3.31 (m, 2H), 4.22 (dd, J=3.7, 12.1 Hz, 1H), 5.02 (t, J=7.2 Hz, 1H), 7.09–7.16 (m, 3H), 7.35–7.37 (m, 4H) 7.46–7.48 (m, 1H); MS 540 m/e (M$^+$).

Anal. Calcd. for $C_{28}H_{39}O_3SF_3$
C, 62.19; H, 7.27.
Found: C, 62.13; H, 7.22.

EXAMPLE 23

3-[3-Methyl-7-iodo-3(E)-hexenyl]-1-trifluoromethyl benzene, (17)

To a solution of sulfone 16 (2.6 g, 4.8 mmol) at 0° in methanol (50 mL) containing Na$_2$HPO$_4$ (2.67 g, 18.8 mmoL) is added sodium amalgam (6% sodium). The reaction mixture is warmed to about 23° and stirred for about 4 hours then poured into water and the aqueous layer extracted with ether. The organic extracts are dried (brine, MgSO$_4$) and concentrated. The remaining clear oil is purified by column chromatography with 10% ethyl acetate in hexanes as eluant to give in order of elution the desulfonylated material (1.40 g, 3.63 mmol, 76%) as a clear oil and unreacted starting material 16 (0.47 g, 0.87 mmol, 18%).

The silyl ether (3.5 g, 9.1 mmol) is dissolved in THF (20 mL) and treated with tetrabutylammonium fluoride (15 mL, 15.0 mmol, 1.0 M in THF) and stirred at about 23° for about 1 hour. The reaction mixture is poured into water and the aqueous layer is extracted with ether. The ether extracts are combined, dried over magnesium sulfate and concentrated. The remaining clear oil can be purified by flash chromatography with 15% ethyl acetate in hexanes as eluant followed by 20% ethyl acetate in hexanes to give the alcohol (1.6 g, 5.88 mmol, 73%) as a clear oil: IR(film) 3340, 1450, 1325, 1160, 1125, 1075, 795 cm$^{-1}$; $^1$H NMR (CDCl$_3$) δ 1.23 (t, J=5.0 Hz, 1H, exchanges with D$_2$O), 1.54 (dt, J=14.4, 7.1 Hz, 2H); 1.64(s, 3H), 2.03 (dd, J=7.2, 14.6 Hz, 2H), 2.27 (t, J=8.3 Hz, 1H), 2.74 (t, J=7.8 Hz, 2H), 3.54 (m, 2H), 5.08 (t, J=7.2 Hz, 1H), 7.30–7.42 (m, 2H); MS 272 m/e (M$^+$).

Anal. Calcd. for $C_{15}H_{19}OF_3$ C, 66.16; H, 7.03.
Found: C, 66.12; H, 6.99.

A solution of the alcohol (2.0 g, 7.35 mmol) in dichloromethane (10 mL) at 0° is treated with triethylamine (1.03 mL, 8.1 mmol) then methanesulfonyl chloride (0.59 mL, 7.72 mmol). The reaction mixture is warmed to about 23° and stirred for about 12 hours. The reaction mixture is poured into water and the aqueous layer extracted with dichloromethane. The dichloromethane extracts are dried over magnesium sulfate and concentrated to give the mesylate (2.24 g, 87%, 6.4 mmol) as a clear oil. The oil is dissolved in acetone. NaI (11.0 g, 73.5 mmol) is added and the reaction mixture is heated to reflux for about 2 hours. The mixture is cooled, poured into water and the aqueous layer extracted with ether. The organic extracts are dried (MgSO$_4$) and concentrated to give the iodide 17 (2.24 g, 5.86 mmol, 80%) as a dark red oil.

EXAMPLE 24

1,2-dihydro-2,2,4-trimethyl-6-[[5-methyl-7-[3(trifluoromethyl) phenyl]-4(E)-hexenyl]oxy] quinoline, (18)

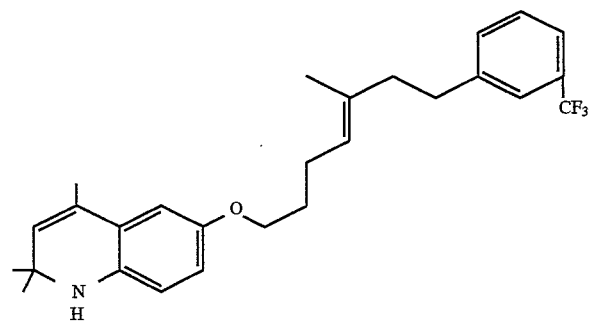

A mixture of phenol 3 (1.2 g, 5.2 mmol), iodide 17 (2.24 g, 5.86 mmol) and K$_2$CO$_3$ (4.0 g, 29.3 mmoL) in DMF (20 mL) is stirred at about 23° for about 1 hour then at about 50° for about 12 hours and at about 90° for about 1 hour. The reaction mixture is cooled, poured into water and the aqueous layer extracted with ethyl acetate. The ethyl acetate extracts are dried over magnesium sulfate and concentrated. The resulting yellow oil is chromatographed to give the Nacetyl derivative (1.72 g, 60%, 3.59 mmol) as a yellow oil contaminated with 0.45 g of an unknown oil that does not interfere with the next reaction: IR (film) 1710, 1670, 1360, 1325, 1200, 1160, 1125, 850 cm$^{-1}$; NMR (CDCl$_3$) δ 1.48 (s, 6H), 1.64 (s, 3H), 1.75 (dt, J =6.9, 13.6 Hz, 2H), 1.98 (s, 3H), 2.10 (s, 3H), 2.13 (q, J=7.6, 14.8 Hz, 2H), 2.28 (t, J=7.8 Hz, 2H), 2.75 (t, J=7.4 Hz, 2H), 3.85 (t, J=6.3 Hz, 2H), 5.52 (t, J=7.1 Hz, 1H), 6.63 (dd, J=2.8, 8.6 Hz, 1H), 6.73–6.77 (m, 2H), 7.29–7.41 (m, 4H); MS 485 m/e (M$^+$).

A solution of the acetamide (1.8 g, 3.7 mmol) in THF (40 mL) maintained at about −78° is treated with LiEt$_3$BH (11.1 mL, 11.1 mmol, 1.0M in THF). The reaction is warmed to about 23° stirred for about 12 hours then poured into water (100 mL) and the aqueous solution extracted with ether. The ether extracts are dried (MgSO$_4$) and concentrated. The yellow residue is purified by column chromatography using 15% ethyl acetate in hexanes as eluant. The free amine is isolated as a light yellow oil (0.4519 g, 1.02 mmol, 28%) and 0.4522 g of an impurity from the previous reaction. Unreduced acetamide (0.817 g, 1.68 mmol, 45%) is also obtained. This procedure is repeated on the acetamide to give (0.105 g, 0.2 mmol, 6%) of unreacted starting material and additional free amine (0.245 g, 0.056 mmol, 14%): IR(film) 3360, 1380, 1325, 1260, 1160, 1125 cm$^{-1}$; $^1$H NMR (CDCl$_3$) δ 1.23 (s, 6H), 1.64 (s, 3H), 1.71 (dt, J=6.8, 13.8 Hz, 2H), 1.95 (br s, 3H), 2.11 (q, J=7.3 , 14.5 Hz, 2H), 2.27 (t, J=7.4,2H), 2.74 (t, 7.4 Hz, 2H), 3.81 (br s, 2H), 5.12 (t, J=7.2 Hz, 1H), 5.4 (br s, 1H), 6.39 (br s, 1H), 6.56 (dd, J=2.5, 8.3 Hz, 1H), 6.66 (br s, 1H), 7.32–7.39 (m, 4H)-(DMSO-d$^6$) δ 1.13 (s, 6H), 1.55–1.60 (m, 2H), 1.59 (s, 3H), 1.84 (s, 3H), 2.04 (dd, J=6.4, 14.5 Hz, 2H), 2.24 (t, J=7.9 Hz, 2H), 2.75 (t, J=7.6 Hz, 2H), 3.70 (t, J=6.3 Hz, 2H), 5.08 (t, J=6.4 Hz, 1H), 5.28 (s, 1H), 5.37 (s, 1H, exchanges with D$_{20}$), 6.36 (d, J=8.1 Hz, 1H), 6.47–6.50 (m, 2H), 7.47–7.51 (m, 4H); MS 443 m/e (M$^+$).

Anal. Calcd. for C$_{27}$H$_{32}$NOF$_3$

C, 73.11; H, 7.27; N, 3.16.

Found: C, 73.15; H, 7.35; N, 3.14.

Other embodiments of the invention will be apparent to the skilled in the art from a consideration of this specification or practice of the invention disclosed herein. It is intended that the specification and examples be considered as examplary only, with the true scope and spirit of the invention being indicated by the following claims.

We claim:

1. A method of inhibiting cholesterol biosynthesis, lowering LDL cholesterol, and inhibiting LDL oxidation which comprises administering to a host in need thereof an effective amount of a compound having the formula

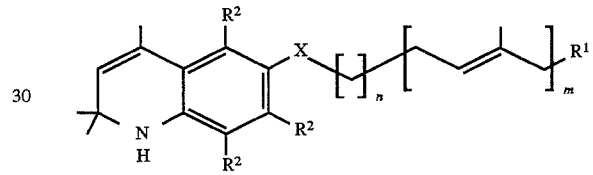

wherein

X is O, S or Ch$_2$

R$^1$ is H or

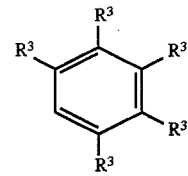

R$^2$ and R$^3$ are independently H, C$_1$–C$_5$ alkyl, CF$_3$, CN, halogen or OCH$_3$, n is an integer of 1 to 3, and m is an integer of 1 to 3, or a pharmaceutically acceptable salt thereof.

2. A method of treating hypercholesterolemia, hyperlipidemia and atherosclerosis which comprises administering to a host in need thereof an effective amount of a compound having the formula

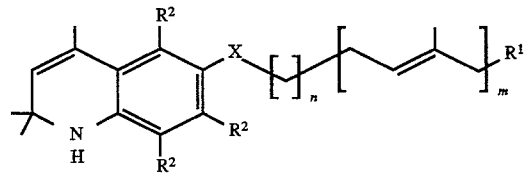

wherein

X is O, S or Ch$_2$ $R^1$ is H or
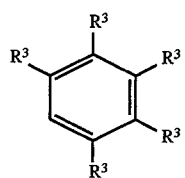
$R^2$ and $R^3$ are independently H, $C_1$–$C_5$ alkyl, $CF_3$, CN, halogen or $OCH_3$,
n is an integer of 1 to 3, and
m is an integer of 1 to 3, or
a pharmaceutically acceptable salt thereof.
* * * * *